(12) United States Patent
Pan et al.

(10) Patent No.: US 10,094,792 B2
(45) Date of Patent: Oct. 9, 2018

(54) METHOD FOR ANALYSIS OF THERMAL RESISTANCE

(71) Applicant: EVERFINE PHOTO-E-INFO CO., LTD., Hangzhou (CN)

(72) Inventors: Jiangen Pan, Hangzhou (CN); Cong Chen, Hangzhou (CN); Yan Huang, Hangzhou (CN)

( * ) Notice: Subject to any disclaimer, the term of this patent is extended or adjusted under 35 U.S.C. 154(b) by 272 days.

(21) Appl. No.: 14/775,127

(22) PCT Filed: Dec. 24, 2013

(86) PCT No.: PCT/CN2013/090321
§ 371 (c)(1),
(2) Date: Sep. 11, 2015

(87) PCT Pub. No.: WO2015/021726
PCT Pub. Date: Feb. 19, 2015

(65) Prior Publication Data
US 2016/0041112 A1  Feb. 11, 2016

(30) Foreign Application Priority Data
Aug. 13, 2013 (CN) .......................... 2013 1 0351643

(51) Int. Cl.
*G01K 17/00* (2006.01)
*G01N 25/18* (2006.01)
(Continued)

(52) U.S. Cl.
CPC .............. *G01N 25/18* (2013.01); *G01N 25/20* (2013.01)

(58) Field of Classification Search
CPC .................................................... G01N 25/18
See application file for complete search history.

(56) References Cited

U.S. PATENT DOCUMENTS

2013/0136151 A1* 5/2013 Chung ............... G01R 31/2642
374/44

FOREIGN PATENT DOCUMENTS

CN   102680512 A    9/2012
CN   102759544 A    10/2012

OTHER PUBLICATIONS

H. Zhang; "Thermal Testing and Simulation of High Power LED;" Chinese Master's Theses Full-text Database; No. 12; Dec. 15, 2009; pp. 1-55, cover sheet, introduction and end sheet (63 pages total).
(Continued)

*Primary Examiner* — Phuong Huynh
(74) *Attorney, Agent, or Firm* — Kratz, Quintos & Hanson, LLP (57) ABSTRACT

The present invention provides a method for analysis of thermal structures, not only to reduce analysis errors caused by temperature measurement errors, but also to get the thermal resistance of contact interfaces and the internal resistance distribution of heat conduction components of a DUT, by establishing a heat conduction model of the DUT, solving and analyzing a mathematic heat conduction model on the basis of temperature data of a heat source and thermal model parameters, thus realizing the accurate quantitative analysis of thermal resistance structure of the DUT, comprehensively evaluating the thermal contact conditions inside the whole DUT, and providing an important basis for improving the heat dissipation design of LED and other devices. The analysis method features in simplicity, high accuracy, high speed, wide application range, etc.

8 Claims, 5 Drawing Sheets

(51) Int. Cl.
*G01N 25/20* (2006.01)
*G06F 11/30* (2006.01)

(56) References Cited

OTHER PUBLICATIONS

X.-L. Zhao, et al.; "Thermal Characteristics Test Based on the Structural Function Theory;" Opto-Electronic Engineering: vol. 38; No. 9; Sep. 2011; (4 Sheets).
G. Chen, et al.; "Measuring thermal resistance for high voltage LED device and module by applying negative bias voltage; Experimental Technology and Management;" vol. 29; No. 4; Apr. 2012; (5 Sheets).
International Search Report for International Application No. PCT/CN2013/090321 dated Apr. 25, 2014.

* cited by examiner

METHOD FOR ANALYSIS OF THERMAL RESISTANCE

BACKGROUND OF THE INVENTION

1. Technical Field

The present invention relates to the test filed of thermal properties, and particularly to a method for analysis of thermal resistance.

2. Description of Related Art

Heat management becomes a hot spot in the filed of device applications in present research. The optical, electrical, color and life characteristics will be influence by heat dissipation characteristic of devices directly. Thermal resistance is an important evaluation criterion for device heat dissipation characteristic, and an accurate structure of thermal resistance is more important for analyzing the effect of heat contact between components of the device and the defects of heat conduction inside the components.

There are some methods for analysis of the thermal resistance structure recently. Because of only basing on temperature data of the DUT, the results of these methods are influenced by temperature measurement accuracy greatly, so for each heat conduction component, the precise thermal resistance can't be obtained and the problems of heat dissipation characteristics and internal defects can't be judged accurately.

What is more important, thermal resistance of the contact interface between heat conduction components can't be obtained by the existing thermal resistance analysis methods. When the contact of the heat conduction components is bad, the thermal resistance of the contact interface will be increased significantly. So, the thermal resistance of the contact interface is not only an important criterion for judging the heat contact status, but also an important characteristic parameter for designing the heat dissipation and improving the heat management. However, influenced by the surface characteristic and the connection layer of each heat conduction component during the test and analysis of the thermal resistance structure, for example, the difficulty in confirming the thickness of the contact surface, irregular shape of connection layer and anisotropy of the materials of the heat conduction contact surface, generally, the thermal resistance is difficult to measure. Thus the effect of heat contact between the components can't be judged accurately and objectively, causing difficulties to the manufacturers and designers to improve the heat dissipation characteristic.

BRIEF SUMMARY OF THE INVENTION

To overcome the defects in the prior arts, the present invention provides a method for analysis of thermal resistance to obtain the thermal resistance of the contact interface between heat conduction components of the DUT by introducing thermal model parameters and combining heat conduction model and temperature change. The analysis method is features in reliability, high accuracy and wide application scope.

In order to solve the above technical problems, the present invention employs the following technical solution:

A method for analysis of thermal resistance, characterized in that device-under-test (DUT) includes heat sources and heat conduction components, and thermal resistance of contact interfaces between the heat conduction components of a device-under-test is analyzed by using temperature change data of the heat source and thermal model parameters of the heat conduction components; comprising the following steps of:

(a) applying power to the heat source and then measuring the change in temperature of the heat source with time;

(b) establishing a heat conduction module of the DUT to determine function relationships between temperature and time of the heat source and between thermal resistance and capacitance along a heat flow path, and then obtaining the distribution data of the thermal resistance and capacitance of the DUT on the heat flow path through solving the function with the temperature change data of the DUT in step (a);

(c) calculating thermal model parameters of each heat conduction component, including values of the thermal resistance and capacitance, according to the direction of the heat flow, and the size and fixed thermal characteristic parameters of each heat conduction component;

(d) analyzing and comparing the distribution data of the thermal resistance and capacitance on the heat flow path of the DUT and thermal model parameters of the heat conduction components to obtain the thermal resistance of the contact interfaces between the heat conduction components.

In the present invention, the heat source of the DUT can produce/release heat directly or indirectly by inputting external power. For example, if the DUT is an LED, the inside PN junction is the heat source and can produce heat directly by inputting power; or if the DUT is a device without inside heat source the heat source is a specified component or surface with input power. In addition, the relative positions of the heat source and more than one heat conduction components can be set flexibly, which means that the heat source can be built in one heat conduction component, or the heat source and heat conduction components are independent structures of the DUT. For example, for a semiconductor LED, the heat source is at least a PN junction in LED chips.

Input some power to the heat source before the temperature test. The power is external electric power or thermal power. External electric power is constant or zero, and the external thermal power is the input source of the constant temperature or constant or zero. The temperature change in the heat source can be measured in the heating time. For instance, after the heat power is applied to the heat source, measure the transient temperature until the heat source reaches the thermal equilibrium. The temperature also can be measured in cooling time. For example, apply the heat power to heat source until reaching thermal balance, and then remove external power, so that the heat power is zero and the temperature of the heat source begins to reduce. Then, measure the transient temperature until the heat source reaches a new thermal equilibrium.

In the present invention, the starting point of the heat conduction is the heat source, and the heat flow path is along each heat conduction component and the contact interface there-between. During the heat conduction, DUT tends to thermal equilibrium, and the temperature and time of the heat source, the thermal capacitance and resistance of the conduction path are in certain functional relationship. So heat conduction model can be established and the function can be obtained according to the process of temperature rise and fall.

The time is from the beginning of the temperature rise/fall to the moment of thermal equilibrium. The temperature change along the time in each moment of this process can be measured. The function relationship is solved according to the temperature change of the heat source to obtain the distribution data of the thermal capacitance and thermal resistance on the heat flow path. As an optimization, in the time segment where the temperature of the heat source changes rapidly, accurate temperature change information of the heat source is obtained by enhancing the measurement frequency of the temperature so as to accurately solve the above function relationship and obtain accurate distribution data of the thermal capacitance and resistance on the heat flow path.

Figure 1:
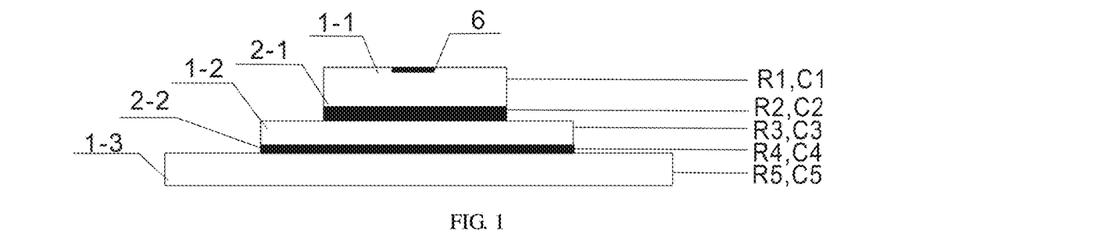
FIG. 1 is a diagram of LED composition.

Take the LED shown in FIG. 1 as an example, the PN junction is the heat source, and the heat conduction structure along each heat conduction component and the contact interface is a one-dimensional heat flow path. Apply constant electric power to the heat source, then the produced heat will take the heat source as the starting point passing through the one-dimensional heat flow path. According to these conditions, establish a CAUER model shown in FIG. 3, which simulates the thermal capacitance and resistance characteristic of n continuous infinitesimals on the one-dimensional heat flow path of the DUT by using n RC networks. In each RC network, $C_{wi}$ and $R_{wi}$ correspond to the thermal capacitance and resistance characteristic of each infinitesimal, and each infinitesimal corresponds to each heat conduction component and contact interface. Get $C_{wi}$ and $R_{wi}$ of each RC network, then the distribution data of the thermal capacitance and resistance in conduction path can be obtained. The CAUER model can be solved by establishing a FOSTER model shown in FIG. 4.

$$T_{(t)} = \Delta P_H \sum_{i=1}^{n} R_{thi} \cdot \left[1 - \exp\left(-\frac{t}{\tau_i}\right)\right]; \tau_i = C_{thi} \cdot R_{thi} \tag{1}$$

Figure 3:
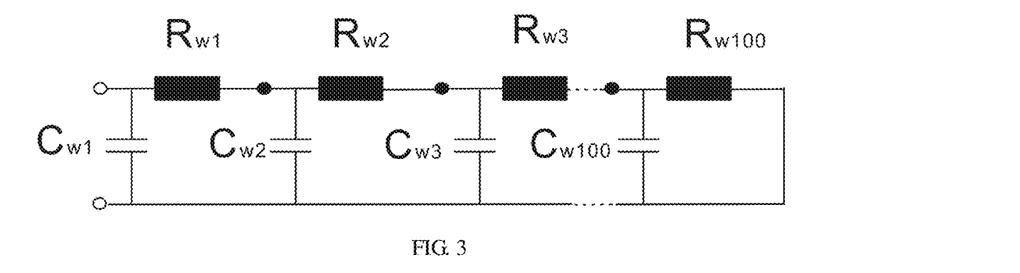
FIG. 3 is a CAUER RC thermal model.
Figure 4:
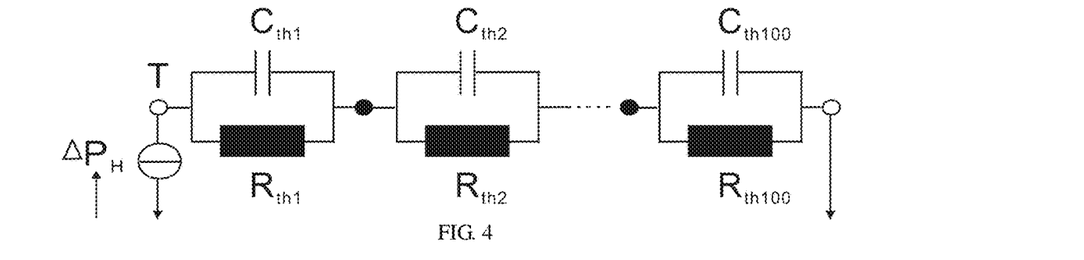
FIG. 4 is a FOSTER RC thermal model.

$T_{(t)}$ is the temperature change in the moment of t compared to the initial moment. $\Delta P_H$ is the heat power. $\tau_i$ is time constant. $C_{thi}$ and $R_{thi}$ are the thermal capacitance and resistance in the FOSTER model. Each value of $C_{thi}$ and $R_{thi}$ can be calculated by combining the above formula with $T_{(t)}$ of at least n moments in the process of the heat source tending to thermal equilibrium through a series of equivalence transformation and deconvolution calculations. Then transform the FOSTER model to the CAUER model, $C_{wi}$ and $R_{wi}$ of each RC network in the CAUER model can be obtained, namely the distribution data of the thermal capacitance and resistance in one-dimensional conduction path. Compare the distribution data with the thermal model parameters of each heat conduction component of DUT, then thermal resistance of the contact interface between the heat conduction components can be obtained. The interface refers to the contact interface between heat conduction components or connecting layer or air gaps.

Thermal model parameters of the heat conduction components, including values of the thermal resistance and capacitance, can be calculated by size, thermal characteristic parameters and heat flow direction of heat conduction components. Take the LED shown in FIG. 1 and FIG. 2 as an example, the PN junction is the heat source, while the chip, metal substrate, MCPCB, etc. are heat conduction components. The heat generated by the PN junction passing through the heat conduction component to perform one-dimensional heat conduction. And the thermal resistance and capacitance of a certain heat conduction component can be determined by the heat flow direction, component size, connection area, specific heat, heat conductivity of material, etc., as follows:

$$C = \int_0^h cv \cdot A(x) \cdot dx \tag{2}$$

$$R \int_0^h \frac{1}{\lambda \cdot A(x)} \cdot dx \tag{3}$$

C is the thermal capacitance, R is the thermal resistance, h is the thickness of the heat conduction component along the one-dimensional heat conduction direction; A(x) is the sectional area at the distance x to the heat source along the heat flow path, cv and λ are the thermal capacitance at constant volume and the heat conductivity of the material of heat conduction components.

In the present invention, the thermal resistance structure function of the DUT can be obtained by the distribution data of the thermal capacitance and resistance on the heat flow path, and thermal model parameters of each component can be calculated by formula (2) and formula (3). According to the thermal model parameters, the corresponding interval, in the structure function, corresponding to each heat conduction component can be located to obtain the corresponding interval of the contact interface between the heat conduction components and obtain the thermal capacitance and resistance of each contact interface by the interval size.

In the present invention, the ratio of the thermal capacitance to thermal resistance of each infinitesimal can be calculated according to the distribution data of the thermal capacitance and resistance on the heat flow path. According to the defining formulas (2) and (3) of the thermal capacitance and resistance, the ratio of the thermal capacitance to thermal resistance of each infinitesimal shall be:

$$\frac{C}{R} = cv \cdot \lambda \cdot A^2(x) \tag{4}$$

For the heat conduction component with uniform composition, the error of the ratio of the thermal capacitance to thermal resistance obtained using the formula (4) should within a certain range. So the infinitesimal on the heat flow path corresponding to each heat conduction component can be confirmed by the thermal capacitance/thermal resistance ratio of the whole component and the thermal capacitance/thermal resistance ratio of each infinitesimal. Due to the infinitesimals on the heat flow path corresponding to the heat conduction components and the contact interfaces in turn and continuously, the infinitesimal corresponding to the contact interfaces can be determined by determining the infinitesimal corresponding to each heat conduction component, so does the thermal resistance value (sum of the thermal resistance of the corresponding infinitesimals).

Compared with the prior art, the present invention can calculate accurate the thermal model parameters according to the material characteristic of each heat conduction component, then analyze the parameters and the structure function together, quantify and separate the thermal resistance of each heat conduction component and the contact interface from the distribution information shown in the structure function, to realize accurate quantitative analysis of the thermal resistance structure. Starting from both the thermal resistance structure function and the thermal model parameters of the DUT, and on the basis of the material characteristics of the DUT, the present invention overcomes the defect of failing to obtain the thermal resistance of the contact interface in the prior art, and can accurately obtain the distribution information of the thermal capacitance and resistance inside the heat conduction component, thus comprehensively analyzing and evaluating the effect of the heat contact and defects of the heat conduction. The present invention features in simplicity, high efficiency, high accuracy, high analysis speed and wide application scope.

Figure 6:
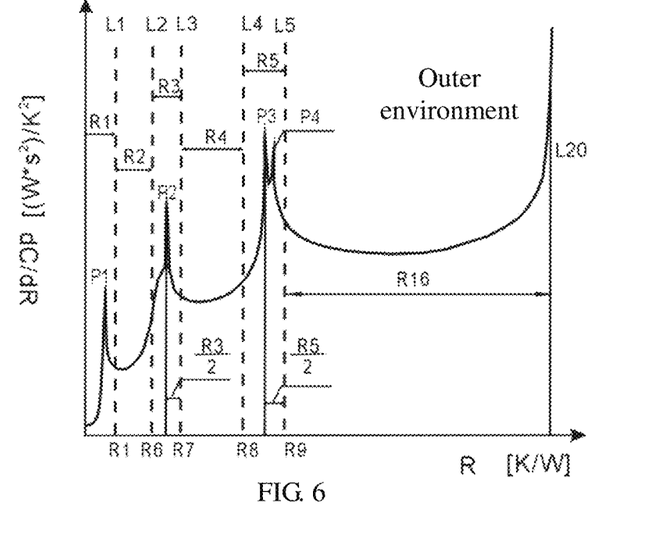
FIG. 6 is a schematic view of embodiment 1.
Figure 8:
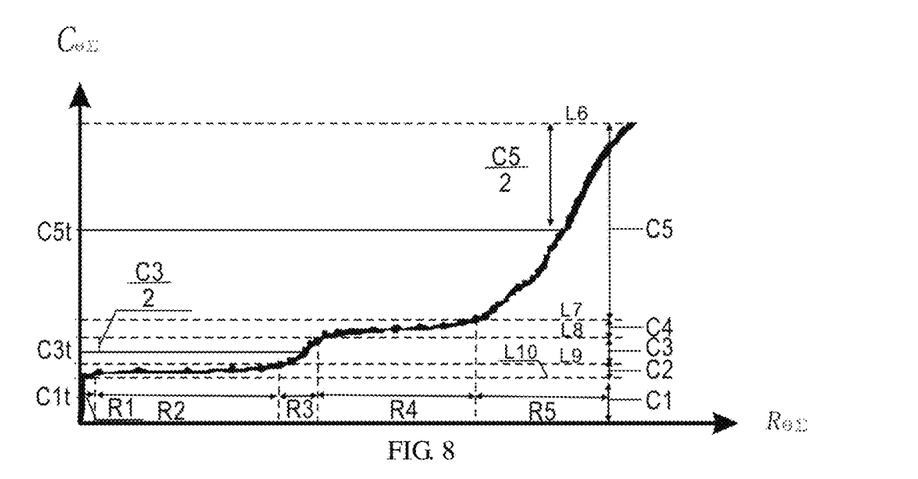
FIG. 8 is a schematic view of embodiment 3.

The present invention can be perfected by the following solution:

In the present invention, according to the distribution data of the thermal resistance and capacitance on the heat flow path, the data change in the cumulative thermal capacitance along with the cumulative thermal resistance at each point from the heat source to the heat flow path can be obtained, namely the thermal resistance structure function of the DUT including the integral and differential structure functions as shown in FIG. 6 and FIG. 8. The integral structure function is variation of the cumulative thermal capacitance along with the cumulative thermal resistance, and the differential structure function is first derivative of the integral structure function to the cumulative thermal resistance. The cumulative thermal capacitance is sum of the thermal capacitance of the points from the heat source to the heat flow path, and the cumulative thermal resistance is sum of the thermal resistance of the point from the heat source to the heat flow path. In the differential structure function, the heat source is the starting point of the heat conduction, each pinnacle of the characteristic peak corresponds to each heat conduction component on the heat flow path. The width of THE characteristic peak depends on the thermal resistance, and the area of the characteristic peak depends on the thermal capacitance. In the integral structure function, the width of the corresponding interval of each heat conduction component depends on the thermal resistance and/or the thermal capacitance of the heat conduction components. Compare the integral/differential structure function with the thermal model parameters of the heat conduction components, then the interval in the structure function corresponding to each heat conduction component can be located to obtain the intervals corresponding to each contact interface, according to which the thermal resistance can be obtained.

In a technical solution, in the differential structure function, determine the corresponding characteristic peak of each heat conduction component then determine the width and boundary of the characteristic peak based on the thermal resistance. The thermal resistance at the boundary corresponds to the cumulative thermal resistance from the heat source to the input or output interface of the heat conduction components. The characteristic peak of the differential structure function corresponds to each heat conduction component in turn. If the heat conduction component of the DUT is homogeneous, take the peak coordinate of the characteristic peak as a midpoint, and plot out the peak boundary at equal distance, or get the peak boundary by existing XP of each heat conduction component. For example, get the distance from the peak boundary to the peak coordinate at a certain scale (as 6:4). If the heat source is inside a heat conduction component, the corresponding characteristic peak is the first peak of thermal resistance structure function, the curve of which takes one end of the peak boundary as the starting point and the width of which is the thermal resistance values.

When there are several peaks adjacent to each other in the characteristic peak of the differential structure function corresponding to the heat conduction components, the peak corresponds to the maximal point in the interval of the function curve corresponding to the heat conduction component, in order to suppress the interference of factors such as the structure defect to analyze the thermal resistance structure. The width of characteristic peak of each heat conduction component depends on thermal resistance value, and the two are of one size. The positions of peak boundaries on two sides are determined according to the material properties or experience methods of each heat conduction component, and the peak width and peak position.

In a technical solution, the peak width and peak area are determined by the characteristic peak. The position of the peak boundary can be confirmed if the difference between the peak area in the set peak width and the thermal capacitance of heat the conduction components is within the set error range. For corresponding characteristic peak of each conduction component in the differential structure function, the peak width is equal to the thermal resistance values, and the peak area is equal to the thermal capacitance. So the peak width is fixed, while the boundary is changing in a certain way. Finally the boundary position will be confirmed, when the difference between the peak area of the characteristic peak and the thermal capacitance of the heat conduction component is minimal. As an optimization, the variety of peak the boundary is limited in an interval, which takes the peak of each characteristic peak as a center and thermal resistance as a half width. When the heat source is inside a heat conduction component, the peak boundary is at the position of the abscissa corresponding to the starting point of the structure function curve and the value of the thermal resistance. This technology applies the values of the thermal resistance and thermal capacitance to the analysis process of differential structure functions, thus the location of the peak boundary is more accurate, and the analysis accuracy of the interface thermal resistance has a huge improvement.

In a technical solution, ascertain characteristic thermal capacitance corresponding to each heat conduction component and the corresponding interval in integral structure function according to characteristic thermal capacitance and thermal capacitance of each conduction component. In integral structure function, find out the point corresponding to apex of characteristic peak in differential structure function, which is the curvature maximal point of a curve corresponding to differential structure function of each heat conduction component, and the corresponding cumulative thermal capacitance in integral structure function is characteristic thermal capacitance of each heat conduction component. According to characteristic thermal capacitance and capacitance of each heat conduction component, the interval corresponding to each heat conduction component in integral structure function can be determined, position of which depends on material properties or experience methods of each heat conduction component. For example, FIG. 8 shows integral structure function of a LED, which has uniform material heat conduction component. Take characteristic thermal capacitance as a center and the half thermal capacitance as a distance to determine the corresponding interval of each heat conduction component on y-axis and x-axis. Further more get the corresponding interval of interfaces between each heat conduction component, and obtain the thermal resistance value.

In a technical solution, the corresponding interval of each heat conduction component in integral structure function depends on characteristic thermal capacitance, thermal capacitance and thermal resistance of each heat conduction component. Take the integral structure function shown in FIG. 9 for example, for heat conduction components, the width of corresponding interval on y-axis is thermal capacitance value, and that on x-axis is thermal resistance value. Fix the corresponding interval width on y-axis, which is the distance between boundary of each interval, and the boundaries move down-up at a certain distance. As a preferred, the move of boundaries on y-axis limit to the range that takes characteristic thermal capacitance as the center and thermal capacitance value of each heat conduction component as the width. When the obtained interval width on x-axis is the nearest to thermal resistance of the heat conduction component, the position of interval boundary can be determined.

In a technical solution, the standard components the same with DUT are included. Test differential structure functions of the standard components and DUT in the same conditions, and calibrate the peak position of the characteristic peak in differential structure functions of the DUT according to the thermal resistance value between the end of the heat conduction of the standard components and test conditions. The composition and thermal resistance structure of the standard components are already known and are the same with DUT. The temperature change in the heat source of the standard components and DUT are measured in the same test environment, such as the static air test box, the thermal resistance of the interface between the end heat conduction of the standard components and DUT and the outside temperature should be the same. For example, the differential structure function shown in FIG. 6 is tested in the static air test box, the thermal resistance of the contact interface between the end of DUT and the outside temperature is R16, which should be the same with the contact interface of the standard components. When the thermal resistance of the contact interface is known, the last characteristic peak P3 in the differential structure function of the DUT can be calibrated based on the thermal resistance to avoid the i error introduced in the measurement process and make the analysis result more accurate.

Another method for analysis of thermal resistance characterized in that the DUT comprises the heat source and more than one heat conduction components; the distribution data of the thermal resistance and capacitance along the heat flow path of the DUT are obtained through establishing a heat conduction module of the DUT, employing the thermal model parameters of each heat conduction component as limit conditions and combining the temperature change in the heat source so as to obtain the thermal resistance of contact interfaces between heat conduction components directly; comprising the following steps of:

(a) applying power to the heat source, and then measuring temperature change in heat source with time;

(b) calculating thermal model parameters of each heat conduction component, including values of thermal resistance and capacitance, according to the direction of the heat flow, the size and fixed thermal parameters of each heat conduction component;

(c) establishing a heat conduction model of the DUT, and determining function relationships between temperature and time of the heat source and between thermal resistance and capacitance of each infinitesimal;

(d) solving the function relationships in step (c) through employing the calculated thermal model parameters of each heat conduction component as the limit conditions of the heat conduction model and combining the temperature change in the heat source with time to obtain the distribution data of the thermal capacitance and resistance along the heat flow path of the DUT, and to obtain the thermal resistance of the contact interface between the heat conduction components directly.

Take the heat source of the DUT as the starting point of the heat conduction, and divide each heat conduction component of the DUT and the contact interface between heat conduction components into continuous and finite heat conduction infinitesimal elements along the heat flow path. Changes in the heat source temperature of the DUT depend on the thermal capacitance and the resistance of each heat conduction infinitesimal element along the heat flow path. Then the heat conduction model corresponding to the heat conduction process can be established to confirm the function relationships between the temperature and time of the heat source and between the thermal capacitance and resistance of each infinitesimal element. In this technical solution, one heat conduction component corresponds to one or more continuous heat conduction infinitesimal elements along the heat flow path, meaning that the thermal resistance corresponding to the thermal resistance of one infinitesimal element or the sum of several infinitesimal elements, so is the thermal capacitance. Therefore, through determining the infinitesimal element corresponding to each heat conduction component and by combining the temperature variation data of the heat source, the heat conduction model can be calculated with the dual direction as basis of the temperature data and the thermal model parameters to reduce the analysis error caused by the temperature measurement error. This can also improve the analysis accuracy of thermal resistance.

Take the LED shown in FIG. 1 as an example, the PN junction is the heat source, and the heat conduction structure consisting of each heat conduction component and the contact interfaces between the heat conduction components is regarded as the one-dimensional heat flow path. Input power to the heat source, then the produced heat uses the heat source as a starting point. Then the one-dimensional heat flow path consisting of the each heat conduction component and the contact interfaces between the heat conduction components as heat conduction to establish a heat conduction model shown in FIG. 3, which simulates n finite heat conduction infinitesimal elements by using n finite RC networks. This technical solution takes the thermal model parameters (thermal resistance and thermal capacitance) of each heat conduction component as a limiting condition to determine the corresponding one or more RC networks, and thermal resistance is the thermal resistance sum of the corresponding one or more infinitesimal element, so is the thermal capacitance. Based on this limit condition, and the function relationships between the temperature and time of the heat source and between the thermal capacitance and thermal resistance of each infinitesimal element, and according to the temperature variation data in the process of the heat source tending to the thermal equilibrium, and the thermal model parameters of each heat conduction component, the equation set can be solved to obtain $R_{wi}$, $C_{wi}$ of each RC network. The thermal capacitance and resistance of each contact interface can be got directly according to those of the corresponding infinitesimal element. Or, the thermal resistance structure function is obtained by $R_{wi}$, $C_{wi}$ of each RC network, while cumulative thermal capacitance in structure function is obtained by adding the thermal capacitance values of infinitesimal elements in turn, as is the cumulative thermal resistance. When the corresponding infinitesimal element of each heat conduction component is determined, then a curve in the structure function is determined, the curve corresponding to each contact interface is also determined, and the thermal resistance of each contact interface can be directly read from the structure function.

In the present invention, the thermal model parameters of each heat conduction component can be the thermal capacitance and resistance of the whole component obtained through simulating calculation according to formulas (2) and (3), or the thermal capacitance and thermal resistance of each structure unit of the heat conduction components. Divide each heat conduction component into finite units along the heat flow direction according to the material properties. Each structure unit corresponds to one or more heat conduction infinitesimal elements on the heat flow path. In such circumstances, the thermal model parameters are the thermal resistance and thermal capacitance of each structure unit by obtained by simulating calculation by using formulas (2) and (3) according to the geometric information and material properties of each heat conduction component. In this solution, the number of the infinitesimal element corresponding to each heat conduction component shouldn't be smaller than the number of structure units. In order to obtain the relationship between the thermal model parameters and the thermal capacitance & thermal resistance of the corresponding infinitesimal element, each structure unit corresponds to one or more continuous infinitesimal elements on one-dimensional heat flow path. Combined with temperature variation data of the heat source, the equations built on the basis of the heat conduction model can be solved. Through division of the components into several structure units and simulative calculation of the thermal model parameters of each structure unit, distribution information of the thermal capacitance and resistance inside the heat conduction components can be directly obtained, and corresponding each structure unit to an infinitesimal element. The thermal capacitance and resistance of each infinitesimal element corresponding to the heat conduction component can be obtained directly, which makes the solution of equations simpler, more accurate, and more efficient.

For example, if the heat conduction component has an irregular shape or is composed of multilayer materials, the component can be divided into finite structure units according to the structure and the boundary of composite layer, and the thermal model parameters can be obtained through simulative calculations according to the material properties of each structure unit. Currently, each structure unit is corresponded to one infinitesimal element, and evenly corresponds to the rest of the infinitesimal elements to contact interfaces. If the DUT consists of three heat conduct components and two interfaces there-between, the heat flow path can be divided into 60 infinitesimal elements, and the three heat conduction components are divided into 10 structure units uniformly. The first heat conduct component corresponds to infinitesimal elements 1 to 10; the first interface corresponds to infinitesimal elements 11 to 25; the second heat conduction component corresponds to infinitesimal elements 26 to 35; the second interface corresponds to infinitesimal elements 36 to 50; and the third heat conduction component corresponds to infinitesimal elements 51 to 60. Insert the thermal mode parameters of each structure unit into the heat conduction model, and solve the heat conduction model by using the temperature change data of the heat source, and then thermal resistance of each interface can be obtained which much fewer calculations.

In the present invention, the structure unit may be any known geometric unit with a regular (such as cuboid) or an irregular (such as polyhedron) shape, or a vaulted structure with a certain radian, as long as the thermal model parameters can be calculated with formulas (2) and (3).

The above two methods of the present invention can be both further defined and perfected by the following t technical solutions:

In a technical solution, place the DUT or the heat conduction end of the DUT in a natural convection environment or controllable constant temperature environment during the measurement of the heat source temperature. The environment where the heat conduction end is located is required to be stabilized and has the heat absorption capacitance not lower than that of other environment where other parts are located. When the DUT is placed in the natural convection environment, the ambient temperature is the same with that of the surfaces contacting the outside environment directly, including the heat conduction end of the DUT. When the DUT is placed in the controllable constant temperature environment, the ambient temperature is promptly adjustable to not be lower than the ambient temperature of the environment where other parts are located. In this way, the heat exchange in different directions generated by uneven temperature of heat conduction end can be reduced; the heat can flow from the heat source to each point of the heat conduction end, similar to assumed heat conduction process in the heat conduction model. In addition, stable temperature environment can avoid influences of the fluctuation of the outside ambient temperature on measurement of the heat source temperature of the DUT, thus improving the analysis accuracy of the structure function in many ways. As an optimization, different devices can be applied to different ambient temperatures.

Figure 12:
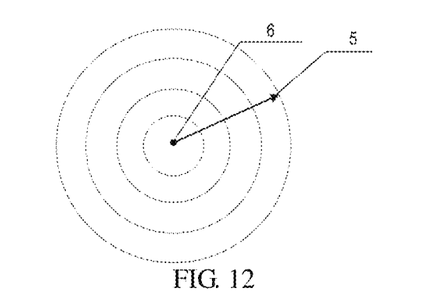
FIG. 12 is a heat conduction diagram of a device.
Figure 13:
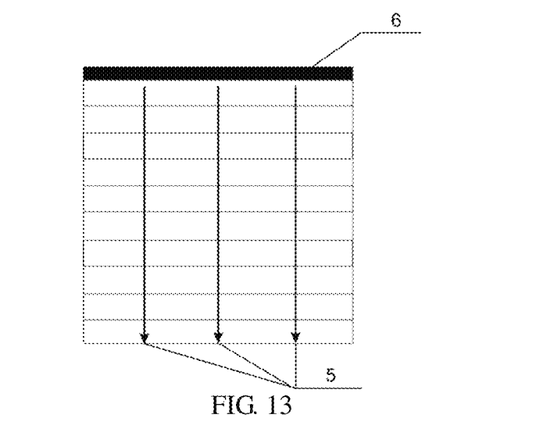
FIG. 13 is a heat conduction diagram of the other device;
1—heat conduction component; 1-1—chip; 1-2—metal substrate; 1-3—aluminium substrate; 2—contact interface; 2-1—the first contact interface;
2-2—the second contact interface; 3—heat flow input interface, 4—heat flow output interface, 5—heat flow path, 6—heat source.

For example, for a round disc component as shown in FIG. 12, if the heat conduction model of the round disc component is established on the basis of then one-dimensional heat conduction theory, and the heat source is located in the center, then the round disc component can be tested in the static air test box. At this time, the round edge at the heat conduction end is isothermal approximately, and the heat flows from the heat source to each point of the edge, which approaches to the process of the one-dimensional heat conduction. For the structure of the component with a structure as shown in FIG. 1, the heat source can be considered as the heat conduction surface with uniform heat flux density on surface of the component, and other parts can be seen as dissipation structures as shown in FIG. 13. If the heat conduction model of the component is established on the basis of the one-dimensional heat conduction theory, the component is tested on a heat sink. Here the lower surface of the component directly contacts with heat sink, which approaches to the isothermal heat conduction surface. The heat flows from the upper surface to the lower surface evenly. The heat flow directions are all perpendicular to each heat conduction surface, and the heat conduction process also tends to the one-dimensional heat conduction. Getting the temperature data of the heat source under this condition can solve the one-dimensional heat conduction model, and then the accuracy distribution information of thermal capacitance and resistance can be obtained.

The present invention also can obtain accurate temperature data of the designated heat conduction model by setting different temperature measurement environments. Take the component shown in FIG. 13 an as example, the heat on the heat source flows to the heat conduction end along the one-dimensional heat flow path composed of the heat conduction components and each interface, and the end of heat conduction is placed on heat sink. At this moment, heat insulators can be laid on the upper surface and 4 lateral surfaces of stereostructure to reduce the heat exchange between other outer surfaces beside the heat conduction end and the environment, so that the heat conduction process therein approaches the one-dimensional heat conduction to accurately solve the one-dimensional heat conduction model.

Given all that, the present invention has the following beneficial effects: by applying the thermal model parameters of each heat conduction component to the analysis of the DUT thermal resistance structure model and the thermal resistance structure function, the analysis error which is caused by the temperature measurement error can be reduced. In addition, the thermal resistance of the DUT interface and the precise inner distribution of each heat conduction components and heat conduction model bidirectionally based on temperature data and thermal model parameters can be obtained. Therefore, realizing the quantitative analysis of the DUT thermal resistance structure provides an important basis for identification of the heat conduction defects inside the DUT. The method can be widely used for thermal resistance analysis of various devices, such as diodes, triodes and other semiconductor devices, and the analysis results can be corrected by using similar standard devices. The method features in simplicity d, high accuracy, high speed, wide application scope, etc.

DETAILED DESCRIPTION OF THE INVENTION

Embodiment 1

As shown in FIG. 1, in this embodiment, the DUT is an LED, consisting of a PN junction, a chip (1-1), a first contact interface (2-1) and an aluminum substrate (1-3). As the heat source 6 of LED, the PN junction is located in the chip (1-1). The first contact interface (2-1) and second contact interface (2-2) are connecting layer of different materials and shapes respectively.

Figure 2:
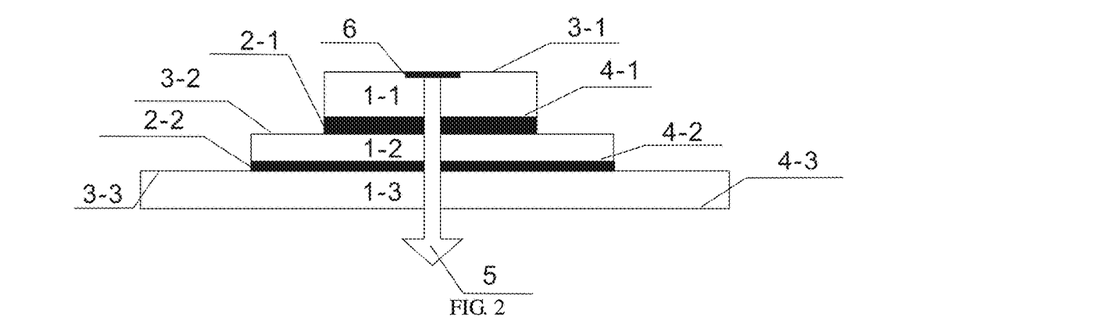
FIG. 2 is a heat conduction diagram of LED.

The heat conduction process of the LED is equivalent to the one-dimensional heat conduction, as shown in FIG. 2. The heat produced by the PN junction on chip (1-1) flows through the chip (1-1), the first contact interface (2-1), metal substrate (1-2), the second contact interface (2-1) and aluminum substrate (1-3) in turn along the one-dimensional heat flow path 5 as shown in the figure. The upper and lower surfaces of the chip (1-1), metal substrate (1-2) and aluminum substrate (1-3) are respective heat conduction interfaces, and the upper surface is the heat flow input interface (3), while the lower surface is the heat flow output interface (4).

The chip (1-1), metal substrate (1-2) and aluminum substrate (1-3) are all of uniform structures with cuboids, and the thermal capacitance (marked as CV1, CV2 and CV3 respectively), thermal conductivity marked as $\lambda 1$, $\lambda 2$, and $\lambda 3$ respectively), contact surface area (marked as A1, A2 and A3) and thickness (marked as D1, D2 and D3) of the three part materials are known. According to the following formula, the values of the thermal capacitance (marked as C1, C3 and C5) of heat conduction component 1 and thermal resistance (marked as R1, R3 and R5) can be calculated.

$$C = cv \cdot d \cdot A$$
$$R = \frac{d}{\lambda \cdot A}$$

Based on the one-dimensional heat conduction process of the LED, CAUER model as shown in FIG. 3 can be established. The thermal capacitance and resistance properties of 100 continuous infinitesimal elements on the one-dimensional heat flow path of the DUT with can be simulated by 100 RC networks. $C_{wi}$ and $R_{wi}$ of each RC network correspond to the thermal capacitance value and thermal resistance of each infinitesimal element on the one-dimensional heat flow path, and the infinitesimal elements on the one-dimensional heat flow path correspond to each heat conduction component (1) and the contact interface (2) on the heat flow path successively. Get $C_{wi}$ and $R_{wi}$ of each RC network in the CAUER model, then the distribution data of the thermal capacitance and thermal resistance on the heat flow path can be obtained.

The CAUER model can be obtained by solving the FOSTER model established as FIG. 4. The model contains 100 RC networks, the thermal capacitance and thermal resistance of each RC network can be marked as $C_{wi}$ and $R_{wi}$ ((i=1, 2, ..., 100). Input certain heating power $\Delta P_H$ to the PN junction of the DUT, then the temperature and time of the heat source, the thermal capacitance $C_{thi}$ and thermal resistance $R_{thi}$ of each RC network can meet the following relations:

$$T_{(t)} = \Delta P_H \sum_{i=1}^{n} R_{thi} \cdot \left[1 - \exp\left(-\frac{t}{\tau_i}\right)\right]; \tau_i = C_{thi} \cdot R_{thi}$$

In the above formula, the time t is heating time. By combining 100 test temperature rise data in the process that heat source trends to the heat balance and through a series of equivalent transformation and deconvolution, each $C_{wi}$ and $R_{wi}$ can be solved. Transform the FOSTER model to the corresponding CAUER model, $C_{wi}$ and $R_{wi}$ of each RC network can be obtained. For the CAUER model, the cumulative thermal capacitance of the thermal resistance structure function can be obtained by adding the thermal capacitance values of the RC networks, and the cumulative thermal resistance of the thermal resistance structure function can be obtained by adding the thermal resistance of RC networks, as shown in FIG. 6.

FIG. 6 shows the heat resistance differential structure function of the DUT, characteristic peaks (marked as P1, P2, P3 and P4) correspond to the chip (1-1), metal substrate (1-2) and aluminum substrate (1-3) respectively from left to right. The boundary of each characteristic peak P is determined by the peak position and the thermal resistance of each heat conduction component. The specific method is as follows: in differential structure function; the characteristic peak corresponding to chip (1-1) is P1; the thermal resistance of chip (1-1) is R1; the left peak boundary of P1 is y-axis; the right peak boundary is L1; and the x-axis of L1 is R1. The characteristic peak of the metal substrate (1-2) is P2. The x-coordinates of P2 are taken as symmetric points to draw two dividing lines L2 and L3 at the distance of $$\frac{R3}{2}$$

to the left and right respectively. The thermal resistance R6 corresponding to x-x-coordinate of L2 is the cumulative thermal resistance between the PN junction and the heat flow input interface 3 of the metal substrate (1-2). The thermal resistance R2 of the first contact interface (2-1) is R6-R1.

The characteristic peak of the aluminum substrate (1-3) should be the maximal point within the region on right of L3, which is the peak P3 with the maximum peak value. The x-coordinates of peak P3 are taken as symmetric points to draw two dividing lines L4 and L5 at the distance of $$\frac{R5}{2}$$

to the left and right respectively. The thermal resistance R8 corresponding to the x-coordinates L4 is the cumulative thermal resistance between the PN junction and heat flow input interface of the aluminum substrate (1-3), and the thermal resistance R7 corresponding to the x-coordinates of L3 is the cumulative thermal resistance between the PN junction and the heat flow input interface of the metal substrate (1-2). The thermal resistance R4 of the second contact interface (2-2) is R8-R7.

According to the above steps, thermal resistance of the chip 1-1, the first contact interface 2-1, metal substrate 1-2, the second contact interface 2-2 and aluminum substrate 1-3: R1, R2, R3, R4 and R5, namely the thermal resistance structure of the DUT, can be obtained. According to the thermal resistance of the heat conduction component 1 and the contact interface 2, and the material characteristics of the DUT, it can be speculated that whether the thermal contact inside the DUT is good or not. For example, large thermal resistance of the contact interface 2 shows the poor contact between the adjacent chip 1-1 and metal substrate 1-3, such as the existence of gaps or bubbles. Alternatively, comparing thermal resistance structures of different DUTs can help the user select products with good thermal contact.

Embodiment 2

Figure 7:
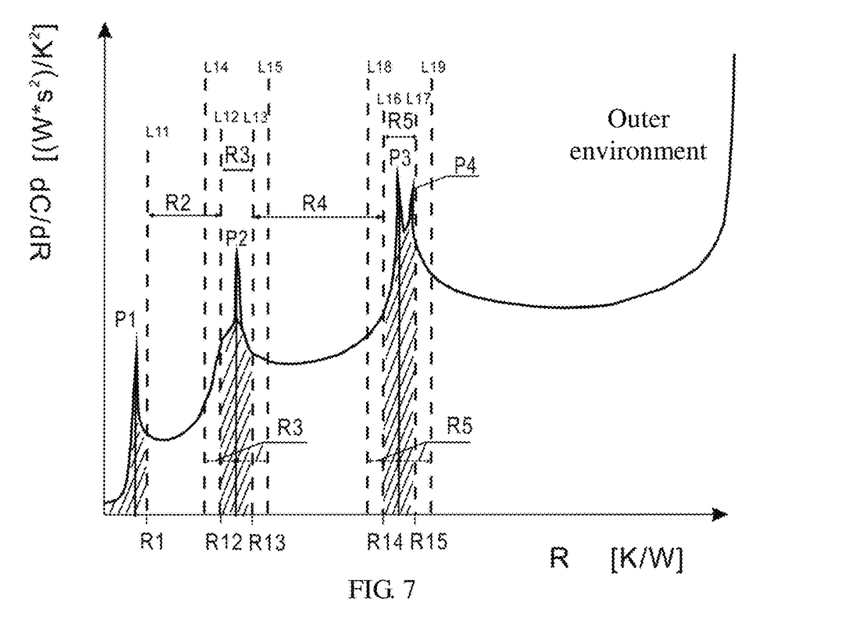
FIG. 7 is a schematic view of embodiment 2.

Different from embodiment 1, in embodiment 2, the position of the peak boundary is determined by comparing the area of the each characteristic peak with a designated width with the thermal capacitance value of each heat conduct component 1. The specific method is as follows.

In a differential structure function as shown in FIG. 7, characteristic peaks corresponding to the chip 1-1, metal substrate 1-2 and aluminum substrate 1-3 respectively are P1, P2 and P3. Theoretically, the area of each characteristic peak P is equal to the thermal capacitance value of the corresponding heat conduction component 1.

The characteristic peak corresponding to the chip 1-1 of the LED is P1; the left boundary of the peak is y-axis, and the corresponding x-coordinates of the right boundary L11 are R1.

The characteristic peak corresponding to the metal substrate 1-2 of the LED is P2. The –coordinates of the peak are taken as symmetric points to draw two divisions L14 and L15 at the distance of R3 to the left and right respectively. In the region between the dividing lines L14 and L15, boundaries L12 and L13 of the characteristic peak P2 move from the left to the right with an interval $$\frac{R3}{10}$$

by a fixed peak width R3. The area of the characteristic peak P2, namely the shadow area as shown in FIG. 7 is calculated after each time of movement. When the calculated peak area is closest to the thermal capacitance value of the metal substrate 1-2, the positions of L12 and L13 as used as the boundary of the characteristic peak P2. The boundary of the characteristic peak P3 is obtained in the similar way. In order to get more accurate results, the movement interval should be as small as possible.

The x-coordinates corresponding to the left peak boundary of each characteristic peak are the cumulative thermal resistance between the PN junction of the LED to the heat flow input interface 3 of each heat conduction component. The x-coordinates corresponding to the right peak boundary are the cumulative thermal resistance between the PN junction of the LED to the heat flow output interface 4 of each heat conduction component. As shown in FIG. 7, the cumulative thermal resistance corresponding to L12, L13, L16 and L17 is R12, R13, R14 and R15 respectively; the thermal resistance R2 of the first contact interface 2-1 is R12-R1, and the thermal resistance R4 of the second contact interface 2-2 is R14-R13.

According to the above steps, thermal resistance of the chip 1-1, the first contact interface 2-1, metal substrate 1-2, the second contact interface 2-2 and aluminum substrate 1-3: R1, R2, R3, R4 and R5, namely the thermal resistance structure of the DUT, can be obtained.

Embodiment 3

Different from embodiment 1, in embodiment 3, the thermal resistance of the contact interface 2 is obtained by comparing the thermal capacitance of each heat conduct component 1 with the integral structure function. The specific method is as follows.

FIG. 8 shows the heat resistance integral structure function of LED. The x-coordinates of the integral structure function are the cumulative thermal resistance of the PN junction of the LED and each heat conduct component 1 or the contact interface 2, and y-coordinates are the cumulative thermal capacitance of the PN junction of the LED and each heat conduct component 1 or the contact interface 2. Each section of the curve corresponds to the chip 1-1, the first contact interface 2-1, metal substrate 1-2, the second contact interface 2-2 and aluminum substrate 1-3 from the left to right.

As shown in FIG. 8, in the integral structure function, each point corresponding to the apex of the characteristic peak in the differential structure function is found out first. The cumulative thermal capacitance value corresponding to each point is the characteristic thermal capacitance C1t, C3t and C5t of each heat conduct component 1. The thermal capacitance value of the chip 1-1 of the LED is C1. The dividing line L10 parallel to the x-coordinates is obtained at y-coordinate C1. The corresponding cumulative thermal capacitance and cumulative thermal resistance at intersection of L10 and the integral structure function are the cumulative thermal capacitance and cumulative thermal resistance of the PN junction of the LED and the heat flow output interface 4-1 of the chip 1-1. The characteristic thermal capacitance C3t is taken as symmetric points to draw two dividing lines L8 and L9 at the distance of $$\frac{C3}{2}$$

up and down along the y-axis respectively. The curve limited by L9 and L10 is the characteristic curve of the first interface 2-1, and the width of this curve corresponding to the x-axis is thermal resistance R2 of the first interface 2-1. Dividing lines L6 and L7 can be obtained by the similar way. The curve limited by L6 and L7 is the characteristic curve of the second contact interface 2-2, the width of which corresponding to the x-axis is the thermal resistance R4 of the second contact interface 2-2.

According to the above steps, the thermal resistance of the chip 1-1, the first contact interface 2-1, metal substrate 1-2, the second contact interface 2-2 and aluminum substrate 1-3: R1, R2, R3, R4 and R5, namely the thermal resistance structure of DUT, can be obtained.

Embodiment 4

Figure 9:
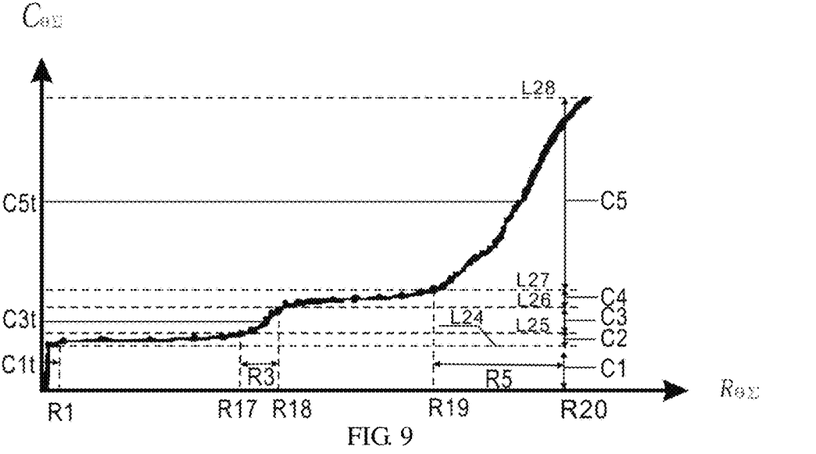
FIG. 9 is a schematic view of embodiment 4.
Figure 10:
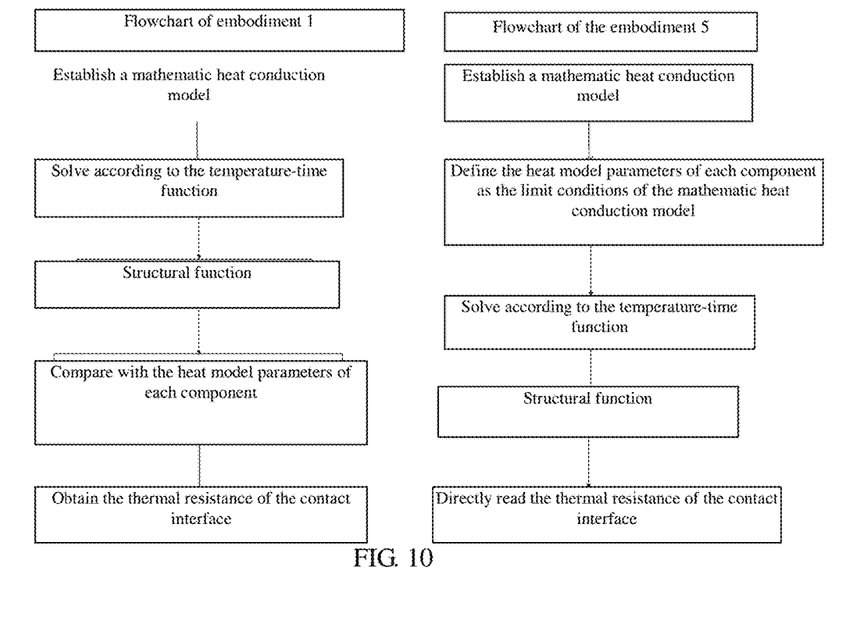
FIG. 10 is an analytical flow diagram of embodiment 1 and 5.

Different from embodiment 3, in embodiment 4, the corresponding region of each heat conduct component 1 in the integral structure function is determined according to the characteristic thermal capacitance value, thermal capacitance value and thermal resistance. The specific method is as follows.

As shown in FIG. 9, in the integral structure function, the characteristic thermal capacitance value of the chip 1-1 of the LED is C1t and the thermal capacitance value is C1. The dividing line L24 that is parallel to the x-axis can be obtained at the coordinate C1. The cumulative thermal capacitance and cumulative thermal resistance corresponding to the intersection of L24 and the integral structure function are the cumulative thermal capacitance and cumulative thermal resistance from the PN junction of the LED to the heat flow output interface 4-1 of chip 1-1. The characteristic thermal capacitance of the metal substrate 1-2 is C3t, and the thermal capacitance is C3. In a region taking C3t as the centre and C3 as a half width, the dividing line L25 takes L24 as the starting point, and keeps a C3 distance with L26 to move from the bottom up. When the interval width of the curve limited by the two dividing lines corresponding to the x-axis is closest to R3, L25 stops moving and the positions of L25 and L26 are determined. The curve limited by L25 and L24 is the characteristic curve of the first contact interface 2-1, and the interval width of the curve corresponding to the x-axis is the thermal resistance R2 of the first contact interface 2-1. The dividing lines L27 and L28 corresponding to the aluminum substrate 1-3 respectively can be obtained by the similar way. The curve limited by L27 and L26 is the characteristic curve of the second contact interface 2-2, and the interval width of the curve corresponding to the x-axis is thermal resistance R4 of the second contact interface 2-2.

The value of cumulative thermal capacitance is big, so the calculation accuracy is easy to be influenced in the calculation process of structure function. Preferably, the interval dividing line L24 corresponding to the chip 1-1 of the LED can be obtained according to its thermal resistance. First, find out the corresponding point of x-coordinate R1 on the integral structure function, and then draw a dividing line L24 though the point parallel to the x-axis.

According to the above steps, the thermal resistance of chip 1-1, the first contact interface 2-1, metal substrate 1-2, the second contact interface 2-2 and aluminium substrate 1-3: R1, R2, R3, R4 and R5, namely the thermal resistance structure, can be obtained.

Embodiment 5

Figure 5:
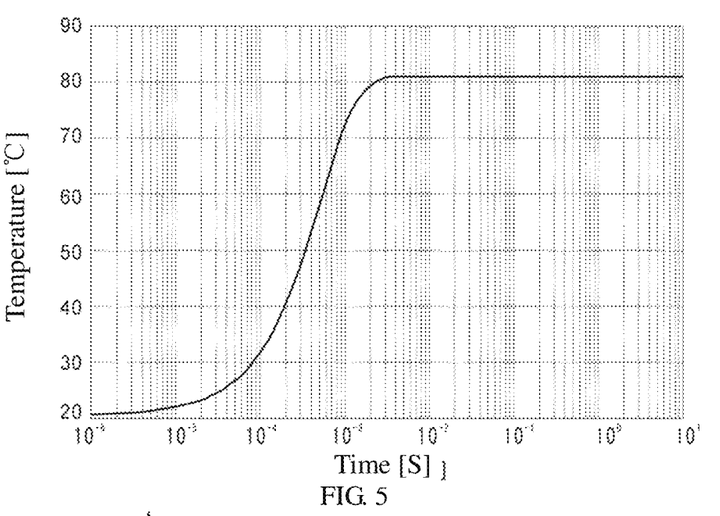
FIG. 5 is a temperature-time curve during temperature rise of a PN junction of the LED.
Figure 11:
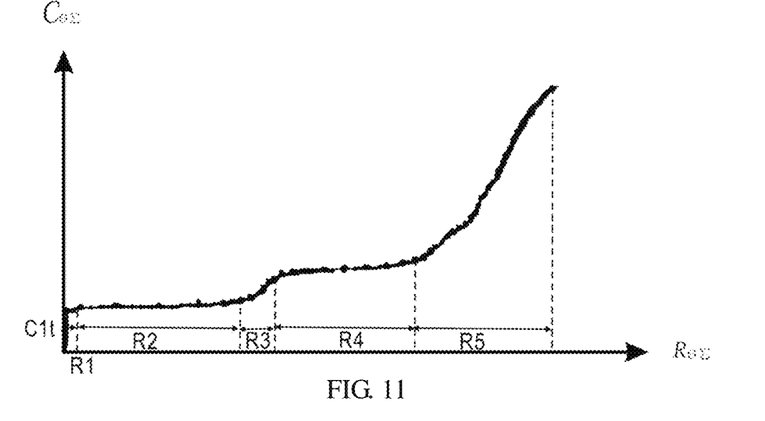
FIG. 11 is a schematic view of embodiment 5.

As shown in FIG. 11, different from embodiment 1, in embodiment 5, each heat conduction component 1 of the DUT is divided into 20 structure units along the heat flow direction, and each structure unit is a heat conduction element corresponding to a RC network of the CAUER model as shown in FIG. 5. Calculate the thermal model parameters of each structure unit, and combine the temperature data change in heating process of the heat source of the DUT, then thermal resistance and thermal capacitance of each RC network in the CAUER model can be calculated, and the thermal resistance of each contact interface 2 can be obtained.

The CAUER model likens the one-dimensional heat flow path comprising of each heat conduction component 1 and the contact interface 2 of the DUT as a 100 order circuit, which is corresponding to the continuous 100 infinitesimals on the heat flow path of the DUT. $C_{wi}$ and $R_{wi}$ of each RC network are the thermal capacitance and thermal resistance of each infinitesimal. In this model, the heat quantity corresponds to the electric quantity; the thermal resistance corresponds to the electric resistance; temperature changes correspond to the potential difference; and heating power corresponds to current. According to the relationship between the physical quantities, the function relationship between the temperature change $\Delta T(t)$ of the heat source corresponding to the initial temperature and the time t, and between the thermal capacitance and thermal resistance of each infinitesimal can be obtained.

In the CAUER model, infinitesimals 1 to 20 correspond to the LED chip 1-1; LED chip 1-1 is divided into 20 structure units, and each structure unit corresponds to the infinitesimals 1 to 20 along the sequence that the heat flows; infinitesimals 20 to 40 correspond to the first interface 2-1. Infinitesimals 41 to 60 correspond to 20 structural units of metal substrate 1-2 in turn; infinitesimals 61 to 80 correspond to the second contact interface 2-2, and infinitesimals 81 to 100 correspond to the 20 structural units of the aluminums substrate 1-3 in turn.

The thermal model parameters of each structure unit can be calculated with the following formula, according to the geometric information and material thermal properties of the heat conduction components of the DUT.

$$C = \int_0^h cv \cdot A(x) \cdot dx$$

-continued $$R = \int_0^h \frac{1}{\lambda \cdot A(x)} \cdot dx$$

C is thermal capacitance; R is thermal resistance; H is thickness of the heat conduction component 1 along the one-dimensional heat conduction direction. A (x) is cross-sectional area located in the heat flow path 5 at distance x with the heat source. Cv and λ are heat capacitance at a constant volume and heat conductivity of the material of the heat conduction component respectively.

According to the above formula, the thermal capacitance and thermal resistance of each infinitesimal corresponding to each structure unit can be calculated, and some unknown quantities of heat conduction in the mathematical heat conduction model can be determined. Combined with the temperature data change of DUT in the process of heat source tendency to heat balance, the thermal capacitance and thermal resistance of each infinitesimal corresponding to each contact interface can be solved speedily: $C_{wi}$ and $R_{wi}$ (i=1, 2, 3 . . . 100), and then thermal resistance of each contact interface can be obtained.

According to thermal capacitance $C_{wi}$ and thermal resistance $R_{wi}$ of the above infinitesimal, the thermal structure function also can be got, as shown in FIG. 11. Points on the structure function from left to right correspond to the infinitesimals 1 to 100 in turn. The curve in structure function corresponding to each heat conduction component 1 and the contact interface 2 of the DUT can be obtained according to the position of each point, and the thermal resistance of the contact interface 2 can be read directly according to the x-axis.

What is claimed is:

1. A method for analysis of thermal resistance, characterized in that a device-under-test (DUT) includes heat sources and heat conduction components, and thermal resistance of contact interfaces between the heat conduction components of the DUT is analyzed by using temperature change data of the heat source and thermal model parameters of the heat conduction components to obtain the thermal resistance of contact interfaces and the internal resistance distribution of heat conduction components of the DUT for allowing a user to modify the material characteristic of each of the heat conduction components of the DUT so as to improve the heat dissipation design thereof, the method comprising the following steps of:
   (a) applying power to the heat source and then measuring the change in temperature of the heat source with time;
   (b) establishing a heat conduction module of the DUT to determine function relationships between temperature and time of the heat source and between thermal resistance and capacitance along a heat flow path, and then obtaining the distribution data of the thermal resistance and capacitance of the DUT on the heat flow path through solving the function with the temperature change data of the DUT in step (a);
   (c) calculating thermal model parameters of each heat conduction component, including values of the thermal resistance and capacitance, according to the direction of the heat flow, and the size and fixed thermal characteristic parameters of each heat conduction component; and
   (d) analyzing and comparing the distribution data of the thermal resistance and capacitance on the heat flow path of the DUT and thermal model parameters of the heat conduction components to obtain the thermal resistance of the contact interfaces between the heat conduction components,
   wherein data change in cumulative thermal capacitance with cumulative thermal resistance at each point from heat source to heat flow path, namely thermal resistance structure function including integral and differential structure function, can be obtained according to distribution data of thermal resistance and capacitance on said heat flow path.

2. A method for analysis of thermal resistance according to claim 1, characterized by determining the corresponding characteristic peak of each heat conduction component in differential structure function, and the width and boundary of the characteristic peak according to the thermal resistance value, wherein thermal resistance at the peak boundary corresponds to cumulative thermal resistance from the heat source to a heat flow input interface or from the heat source to a heat flow output interface.

3. A method for analysis of thermal resistance according to claim 2, wherein the boundary of the characteristic peak is determined by a peak width and a peak area, the location of the peak boundary is determined where the difference between the peak area inside designated width and thermal capacitance of the heat conduction components is within a given error range.

4. A method for analysis of thermal resistance according to claim 1, characterized by determining the characteristic thermal resistance corresponding to each heat conduction component in an integral structure function and determining the corresponding interval of the characteristic thermal resistance value and the thermal resistance value of each heat conduction component in the integral structure function.

5. A method for analysis of thermal resistance according to claim 1, characterized in that the DUT or an end of the DUT is located in natural convective environment or a temperature controllable constant environment during the measurement of the heat source of the DUT.

6. A method for analysis of thermal resistance according to claim 1, characterized in that a standard component analogous to the DUT is further used; comprising: measuring differential structure functions of the standard component and the DUT in the same test environment respectively, and calibrating the position of the characteristic peak of the DUT in the differential structure function according to the thermal resistance between the heat conduction end of the standard apparatus and the test environment.

7. A method for analysis of thermal resistance characterized in that a device-under-test (DUT) comprises the heat source and more than one heat conduction components; the distribution data of the thermal resistance and capacitance along the heat flow path of the DUT are obtained through establishing a heat conduction module of the DUT, employing the thermal model parameters of each heat conduction component as limit conditions and combining the temperature change in the heat source so as to obtain the thermal resistance of contact interfaces and the internal resistance distribution of heat conduction components of the DUT for allowing a user to modify the material characteristic of each of the heat conduction components of the DUT so as to improve the heat dissipation design thereof, the method comprising the following steps of:
   (a) applying power to the heat source, and then measuring temperature change in heat source with time;
   (b) calculating thermal model parameters of each heat conduction component, including values of thermal resistance and capacitance, according to the direction of the heat flow, the size and fixed thermal parameters of each heat conduction component;
(c) establishing a heat conduction model of the DUT, and determining function relationships between temperature and time of the heat source and between thermal resistance and capacitance of each infinitesimal; and
(d) solving the function relationships in step (c) through employing the calculated thermal model parameters of each heat conduction component as the limit conditions of the heat conduction model and combining the temperature change in the heat source with time to obtain the distribution data of the thermal capacitance and resistance along the heat flow path of the DUT, and to obtain the thermal resistance of the contact interface between the heat conduction components directly,
wherein data change in cumulative thermal capacitance with cumulative thermal resistance at each point from heat source to heat flow path, namely thermal resistance structure function including integral and differential structure function, can be obtained according to distribution data of thermal resistance and capacitance on said heat flow path.

8. A method for analysis of thermal resistance according to claim 7, characterized in that the DUT or an end of the DUT is located in natural convective environment or temperature controllable constant environment during the measurement of heat source.

* * * * *